(12) United States Patent
Levin et al.

(10) Patent No.: US 8,965,037 B2
(45) Date of Patent: Feb. 24, 2015

(54) VISUAL INPUT OF VEHICLE OPERATOR

(75) Inventors: Daniel Levin, Gothenburg (SE); Gustav Markkula, Gothenburg (SE)

(73) Assignees: Volvo Car Corporation, Gothenburg (SE); Volvo Technology Corporation, Gothenburg (SE)

(*) Notice: Subject to any disclaimer, the term of this patent is extended or adjusted under 35 U.S.C. 154(b) by 175 days.

(21) Appl. No.: 13/601,789

(22) Filed: Aug. 31, 2012

(65) Prior Publication Data

US 2013/0058529 A1   Mar. 7, 2013

(30) Foreign Application Priority Data

Sep. 2, 2011 (EP) .................................... 11179817

(51) Int. Cl.
  *G06T 7/00*      (2006.01)
  *B60W 50/14*     (2012.01)
  *B60K 28/06*     (2006.01)
  *A61B 3/113*     (2006.01)
  *A61B 5/18*      (2006.01)
  *G06F 3/01*      (2006.01)

(52) U.S. Cl.
  CPC .............. *B60K 28/066* (2013.01); *A61B 3/113* (2013.01); *A61B 5/18* (2013.01); *G06F 3/013* (2013.01)
  USPC .......................................... 382/100; 382/103

(58) Field of Classification Search
  None
  See application file for complete search history.

(56) References Cited

U.S. PATENT DOCUMENTS

| | | |
|---|---|---|
| 2004/0239509 A1 | 12/2004 | Kisacanin et al. |
| 2005/0073136 A1 | 4/2005 | Larsson et al. |
| 2009/0022368 A1* | 1/2009 | Matsuoka et al. ............ 382/103 |
| 2009/0128311 A1 | 5/2009 | Nishimura et al. |
| 2009/0243880 A1 | 10/2009 | Kiuchi |
| 2009/0303078 A1 | 12/2009 | Mochizuki et al. |
| 2010/0033333 A1* | 2/2010 | Victor et al. .................. 340/576 |
| 2012/0268262 A1* | 10/2012 | Popovic ....................... 340/438 |

FOREIGN PATENT DOCUMENTS

EP    1961622 A1    8/2008

OTHER PUBLICATIONS

European Search Report, for EPO Ser. No. 11179317.9-1229, Dec. 16, 2011.
Chen, Jixu et al. "Probabilistic gaze estimation without active personal calibration." Computer Vision and Pattern Recognition (CVPR) 2011 IEEE Conference, Jun. 20, 2011 (pp. 609-616).
European Office Action dated May 8, 2014 issued in corresponding European Application No. 11179817.9.

\* cited by examiner

*Primary Examiner* — Jon Chang
(74) *Attorney, Agent, or Firm* — Harness, Dickey & Pierce, P.L.C.

(57) ABSTRACT

The present invention relates to a method for determining a vehicle operator's visual input of an object in the operator's surroundings, which method comprises receiving an object position signal indicative of the position of at least one object, receiving an operator motion input signal indicative of operator physiological data comprising information relating to body motion of the operator, estimating an operator eye-gaze direction, and determining a visual input quality value representative of level of visual input of the at least one object received by the operator, based on the object position signal and the estimated operator eye-gaze direction.

16 Claims, 8 Drawing Sheets

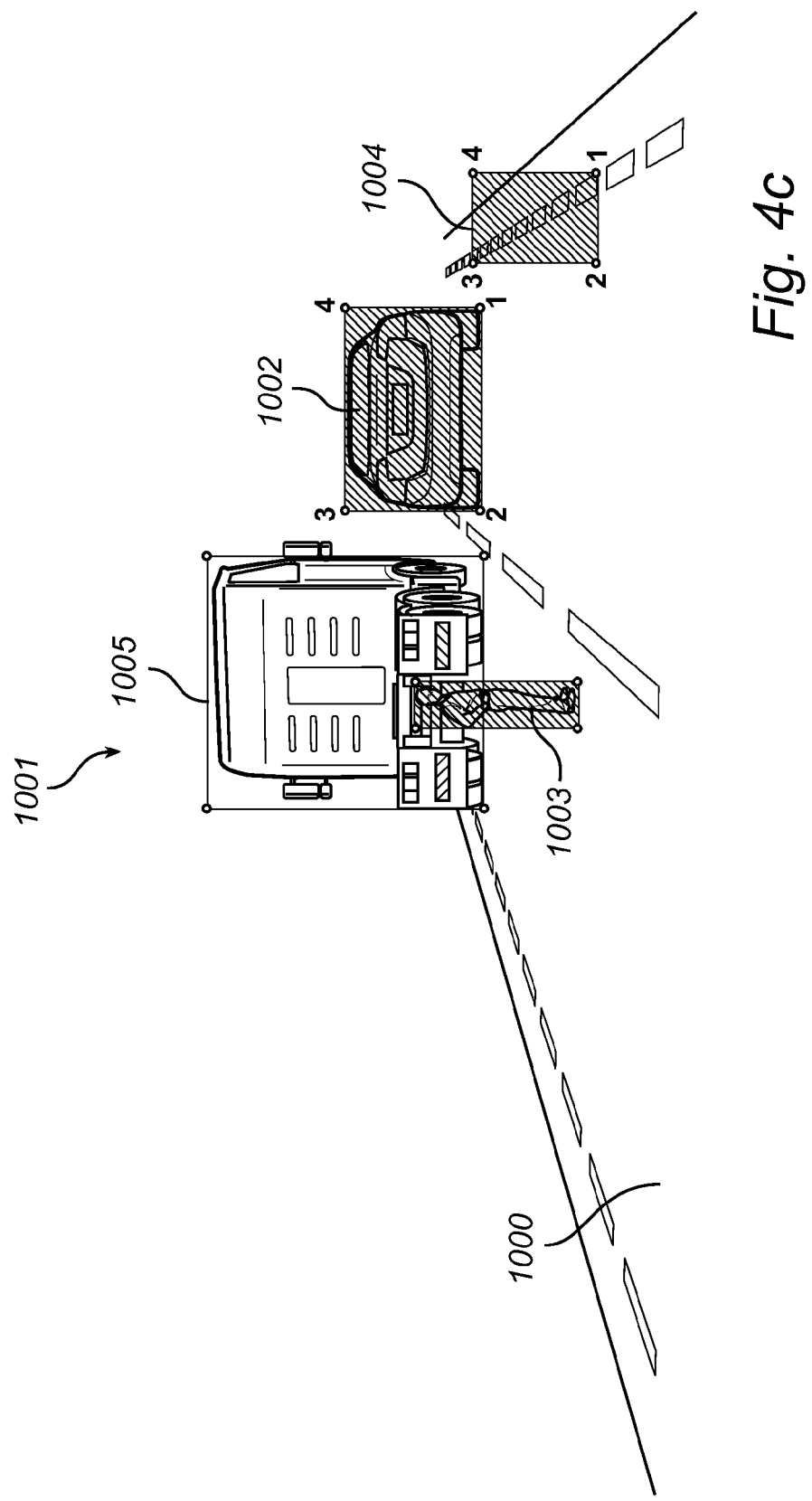

VISUAL INPUT OF VEHICLE OPERATOR

PRIORITY STATEMENT

This claims priority under 35 U.S.C. §119 to European Patent Application No. 11179817.9, filed on Sep. 2, 2011, the contents of which is hereby incorporated by reference in its entirety.

TECHNICAL FIELD

The present invention relates to a method for determining a vehicle operator's visual input of an object in the operator's surroundings, or an operator's visual input of a visual field zone or events occurring within the zone. The present invention also relates to a corresponding system and computer readable medium embodying a computer program product for determining a vehicle operator's visual input of an object in the operator's surroundings. Furthermore, the present invention relates to a method and system for estimating an operator eye-gaze direction of a vehicle operator.

BACKGROUND OF THE INVENTION

Traffic accidents often occur due to the vehicle operator, or driver, not being aware of the surrounding traffic situation. For example, distracted driving is a well known traffic safety problem, and it has e.g. been estimated that a large amount of all road vehicle accidents involve driver distraction.

In order to prevent accidents caused by the operator not being aware of the surrounding traffic situation, it is possible to provide the operator with a warning message to re-establish the attention of the operator to the surrounding traffic situation. However, it is also crucial that a warning system does not warn in situations where the operator is aware of the surrounding traffic situation since such a warning system may cause information overload to the operator, and reduce the level of trust the operator has with regard to the warnings. For example, eye-tracking devices for monitoring the operator's eye during operation are possible. However, eye-gaze direction is difficult to monitor and eye-tracking is often lost.

Hence, there exist a need for a system and a method that provides improved real time in-vehicle estimation of the vehicle operator's attention and/or awareness of the operator's surroundings during operation of a vehicle based on the operator's visual input.

SUMMARY OF THE INVENTION

The object of the present invention is to provide a system and method which allow for improved estimation of a vehicle operator's attention to or visual input from a traffic situation or scene.

According to a first aspect of the present invention, the above may be met by a method for determining a vehicle operator's visual input of an object in the operator's surroundings, the method comprising: receiving an object position signal indicative of the position of at least one object in the operator's surroundings; receiving an operator motion input signal indicative of physiological data comprising information relating to at least one of eye, face, head and body motion of the operator of the vehicle; estimating an operator eye-gaze direction based on the operator motion input signal; and determining a visual input quality value representative of level of visual input of the at least one object received by the operator, based on the object position signal and the estimated operator eye-gaze direction.

According to a second aspect of the present invention, the above may be met by a system for determining a vehicle operator's visual input of an object in the operator's surroundings, the system comprising control means, wherein the control means comprises a first input arranged to receive an object position signal indicative of the position of at least one object in the operator's surroundings; and a second input arranged to receive an operator motion input signal indicative of physiological data comprising information relating to at least one of eye, face, head and body motion of the operator of the vehicle; wherein the control means is arranged to estimate an operator eye-gaze direction based on the operator motion input signal; and arranged to determine a visual input quality value representative of level of visual input of the at least one object received by the operator, based on the object position signal and the estimated operator eye-gaze direction.

The invention is based on the understanding that the vehicle operator's attention of an object may advantageously be estimated in an improved manner by monitoring operator body motion in order to estimate a eye-gaze direction of the operator and use this estimated eye-gaze direction in order to determine a level of attention of the driver, i.e. the visual input quality value, associated with an object or zone in the driver surrounding. In other words, the method and system according to the present invention allows for momentary visual input estimates which are segmented per object, or zone, by estimating an operator eye-gaze direction and mapping this data in relation to a specific object/zone.

Furthermore, the method and system according to the present invention allow for determination of a visual input quality value for objects which are perceived by the operator by direct fixation of the object by the operator's eye, and for objects which are perceived by peripheral vision input by the operator.

For example, the visual input quality value may advantageously be used to represent a momentary estimate of the amount or visual input the operator receives for a plurality of individual traffic objects or zones. The visual input quality value may e.g. be quantified as a number between zero or one, wherein zero is indicative of that the operator currently does not see the object/zone, and wherein the value one is indicative of that the operator receives enough visual input of the object/zone in order to maximally fast obtain a correct understanding of position, movements, velocity and/or derivatives thereof, of objects or events occurring within a certain zone.

The visual input quality value for an object or zone may further be provided to other systems and subsystems of a vehicle and used for e.g. issuing warnings to the operator. Furthermore, advance driver assistance system for the operator of a vehicle, such as collision warning, lane keeping aid, may receive the visual input quality value associated with an object or zone in order to determine how to best influence or assist the driver in relation to a traffic scene or object in the operator's surroundings. The visual input quality value may also be used by in-vehicle information systems in order to evaluate the operator distraction level and to e.g. avoid information overload.

A visual input object may e.g. be a vehicle, pedestrian, road lane, animal, lane marking, road edge, traffic sign, etc. The object may also represent an arbitrary internal or external zone in relation to the vehicle.

By means of the invention, the operator motion input signal may be indicative of a head and/or upper body motion of the operator, such as direction and motion speed and derivatives thereof, wherein the operator eye-gaze is estimated based on the operator motion input signal. Hence, the operator eye-gaze direction may be determined without direct operator eye-gaze direction data from e.g. an eye-tracking device.

For example, the estimated eye-gaze direction may be used when eye-gaze direction data from an eye-tracking device is lost or deactivated. However, the estimated eye-gaze direction may also be based on eye-gaze direction data from an eye-tracking device providing e.g. high detail eye-gaze direction estimations.

According to an exemplifying embodiment, the method and/or system further comprises estimating an expected fixation probability indicative of probability of fixation of the object by the operator's eyes, wherein the step of determining the visual input quality value is further based on the expected fixation probability. The fixation probability allows for classification of different object types. For example, the road lanes markings may be assigned a low fixation probability while persons, such as pedestrians, may be assigned a high fixation probability. Thereby estimating of the visual input quality value for different objects may be based on different estimation processes depending on the fixation probability. For example, the fixation probability may be determined based on size of the object.

According to an exemplifying embodiment, the estimated operator eye-gaze direction comprises a total eye-gaze distribution indicative of probability for different eye-gaze directions of the operator. Hence, the eye-gaze direction of the operator is provides as a probability distribution which spans over the visual field of the operator. For example, the complete visual field of the operator is quantified in to a set of points in a suitable coordinate system, such as visual matrix, wherein each point is assigned probability value according to the total eye-gaze distribution.

According to an exemplifying embodiment, the method and/or system further comprises determining an object area associated with the object, which object area is indicative of the object area of the object as perceived by the operator, wherein the step of determining the visual input quality value is further based on the object area. Thereby, an object in the surrounding traffic situation of the operator is advantageously mapped into the visual perspective of the operator. Hence, the visual input quality value of an object may be determined by evaluating the operator eye-gaze direction in relation to the object area of that object.

According to an exemplifying embodiment, the step of determining the visual input quality value comprises determining a visual acuity distribution indicative of visual acuity level of an eye, or the eyes, of the operator in relation to a center eye-gaze direction, wherein the step of determining the visual input quality value is further based on the visual acuity distribution. By utilizing a visual acuity distribution, the visual input quality value of an object may advantageously be determined based on if the object is fixated by the operator's eyes or rather perceived by the operator's peripheral visual input. The visual acuity distribution defines a center point indicative of a visual acuity peak value associated with the fovea portion of the operator's eyes which is responsible for sharp central vision, wherein the visual acuity value level declines in a direction of increased peripheral vision of the operator, i.e. increased distance from the center point. For example, the visual acuity distribution may be defined as a Gaussian function having a peak at the current, or estimated, eye-gaze direction of the operator may be used.

According to an exemplifying embodiment, the step of determining the visual input quality value comprises integrating the visual acuity distribution over the total eye-gaze distribution over the object area. Thereby, the visual input quality parameter is determined by weighing the visual acuity distribution with the total eye-gaze distribution for all possible eye-gaze directions in the object area.

According to an exemplifying embodiment, the step of determining the visual input quality value comprises convolving the visual acuity distribution with the total eye-gaze distribution in the object area. For example, the visual input quality value may be determined as the maximum value of the convolved total eye-gaze direction distribution and visual acuity distribution within the object area. If the eye-gaze direction distribution and the visual acuity distribution are represented by a respective Gaussian distribution, the convolution will output another Gaussian with known location and extension, wherein the outputted Gaussian distribution, or its location in relation to the object area, and/or the mean value and standard deviation, is/are representative of the visual input quality value of the object.

According to an exemplifying embodiment, the method and/or system further comprises determining a saliency parameter value associated with the object, which saliency parameter is indicative of probability of attracting visual attention. Hence, the visual input quality value may advantageously be determined based on different types of visual stimulus. For example, quick transients, such as abrupt onset of lights, quick movements, certain colors, or high visual contrast of an object, are more likely to attract visual attention of the operator. The visual input quality value of a specific object may e.g. be weighted by the saliency parameter value.

According to an exemplifying embodiment, the object area parameter value comprises at least one pitch and at least one yaw coordinate value in relation to a main head orientation of the operator. For example, the surrounding traffic situation, as perceived by e.g. an external vehicle sensor system in a Cartesian coordinate system may be transformed in a two dimension pitch/yaw coordinate system. Furthermore, the pitch/yaw coordinate system may move with the operator's head movements in pitch and yaw directions.

According to an exemplifying embodiment, the object area parameter value represents an approximated rectangle indicative of the area of the object. For example, the width of the rectangle is approximated by the distance between the two widest points of the object, as perceived by the operator, and may be derived from the object position signal provided by the external vehicle sensor system. The height of the rectangle is approximated by the distance between the vertically highest and lowest points of the object, as perceived by the operator.

According to an exemplifying embodiment, the method and/or system further comprises determining a first eye-gaze direction hypothesis, wherein the total eye-gaze distribution is based on a first eye-gaze direction hypothesis, the hypothesis being indicative of where the operator's eye-gaze direction is aimed. For example, the hypothesis may specify the operator's eye-gaze direction based on easily detectable head or body movements of the operator.

According to an exemplifying embodiment, the method and/or system further comprises determining a second, or a plurality of, eye-gaze direction hypotheses, and determining the total eye-gaze distribution by combining the first and second, or plurality of, eye-gaze direction hypotheses. This is advantageous in that two or more different eye-gaze direction hypothesis may be assessed and evaluated simultaneously in order to output one total eye-gaze distribution.

For example, according to an exemplifying embodiment, the step of estimating the operator eye-gaze direction comprises detecting an operator body movement indicative of a saccade movement of the operator, and estimating a saccade eye-gaze distribution based on the detected operator body movement.

Hence, according to an exemplifying hypothesis, an operator body movement, such as a fast head movement, is detected, wherein it is determined that the fast head movement is indicative of a combined head and eye saccade towards an estimated eye-gaze direction, wherein a saccade eye-gaze distribution is estimated based on that eye-gaze direction.

According to an exemplifying embodiment, the step of estimating the operator eye-gaze direction further comprises determining an eye-gaze time value associated with the saccade eye-gaze distribution, wherein the total eye-gaze distribution is determined based on the saccade eye-gaze distribution and the eye-gaze time value. The eye-gaze time value may advantageously be use for estimating the total eye-gaze distribution by determining for how long time, or to what extent, it is probable that an eye-gaze distribution associated with an eye-gaze direction hypothesis is true. The eye-gaze time value may be further be used for gradually reducing the probability of one eye-gaze direction hypothesis in relation to other eye-gaze direction hypotheses, depending on different initiation times for the different eye-gaze direction hypotheses. For example, the eye-gaze time value correspond to an estimated glance life time associated with a hypothesis, and may e.g. be represented according to a decay model based on e.g. a gamma distribution, or exponential distribution. For example, estimation of glance life time, or whether an eye saccade has been performed since the most recent initiation of an eye-gaze hypothesis, can be modeled according to a decay model. The glance life time is e.g. modeled according to a gamma distribution wherein the life time before decay fallows an approximate normal probability distribution having a peak value corresponds to the most common life time. Furthermore, the approximate normal probability distribution may be fit to match the typical glance life time distribution, wherein an average glance duration/life times may be about 0.5-4 seconds long, or about 1-2 seconds long.

The probability for different eye-gaze direction hypotheses may also approach an equal level over time.

According to an exemplifying embodiment, the step of estimating the operator eye-gaze direction further comprises determining a road-ahead eye-gaze distribution, wherein the total eye-gaze distribution is determined by weighing the saccade eye-gaze distribution with the road-ahead eye-gaze distribution based on the eye-gaze time value. Hence, two separate estimations of eye-gaze direction, or angle, are computed, one for each hypothesis, wherein each hypothesis is represented by an eye-gaze distribution. Each distribution may e.g. be represented by a pitch/yaw value indicative of center eye-gaze direction and pitch/yaw standard deviations.

The road-ahead eye-gaze distribution may e.g. be based on a hypothesis that the operator's eye-gaze direction returns the road-ahead direction after a certain time. For example, the road-ahead eye-gaze direction may be defined as the region with a certain pitch direction, such 10 degree up and 10 degrees down, and within a certain yaw direction, such as 20 degree to the right and 20 degrees to the left, in relation to a center point, or road-ahead far point.

According to an exemplifying embodiment of the system, the control means is further arranged to determine an object area associated with the object, which object area is indicative of the object area of the object as perceived by the operator, wherein the quality value is determined based on the object area.

According to an exemplifying embodiment of the system, the control means is arranged to determine a visual acuity distribution indicative of visual acuity level of an eye of the operator in relation to a center eye-gaze direction, wherein the quality value is determined based on the visual acuity distribution.

According to an exemplifying embodiment, the step of estimating the operator eye-gaze direction further comprises determining if the detected operator body movement indicative of a saccade movement of the operator, such as a combined head and eye saccade movement, is indicative of that the operator eye-gaze is directed towards a road-ahead direction. It may also be determined, according to an exemplifying embodiment, if the detected operator body movement indicative of a saccade movement of the operator, is indicative of that the operator eye-gaze is directed towards an object, or zone, in the operator's surroundings.

For example, according to an exemplifying embodiment, the operator motion input signal is generated by means of an image sensor monitoring the operator.

Moreover, according to an exemplifying embodiment, an object position signal is provided by means of a sensor system. For example, the sensor system comprises a camera, a radar, a lidar, a vehicle-to-vehicle communication device, a vehicle-to-infrastructure communication device, and/or an infrastructure-to-vehicle communication device. Examples of communication devices that may be employed are other vehicles, base stations located along, to the side of, or integrated in the road, or satellites, etc, which may be arranged to transmit information of e.g. position, velocity, acceleration, yaw rate, etc. Road sensors may also provide information of speed limits, road curvature, temperature, road friction properties, etc.

According to an exemplifying embodiment, confidence estimates for the visual quality parameter value is determined for different objects or zones, for example by calculating standard deviations. Confidence estimates from sensors on surrounding objects/zones defined in e.g. Cartesian coordinates may further be transformed into pitch/yaw confidence estimates.

According to a third aspect of the present invention, it relates to a method for determining a vehicle operator's eye-gaze direction during operation of a vehicle, the method comprising receiving an operator motion input signal indicative of physiological data comprising information relating to at least one of eye, face, head and body motion of the operator of the vehicle; and estimating an operator eye-gaze direction based on the operator motion input signal; wherein the estimating of the operator eye-gaze direction is based on a first eye-gaze direction hypothesis.

This aspect of the invention provides similar advantages as discussed above in relation to the previous aspects of the invention.

According to an exemplifying embodiment of the third aspect, it comprises determining a second eye-gaze direction hypothesis, wherein the estimating of the operator eye-gaze direction is based on a first and second operator eye-gaze direction hypothesis. For example, operator eye-gaze direction is estimated by combining the first and second eye-gaze direction hypotheses into a total eye-gaze direction hypothesis indicative of the operator eye-gaze direction.

Furthermore, according to a further exemplifying embodiment, each one of the eye-gaze hypothesis is represented by an eye-gaze distribution indicative of probability for different eye-gaze directions of the operator for that hypothesis. For example, a first eye-gaze hypothesis is represented by a first eye-gaze distribution, and a second eye-gaze hypothesis is represented by a second eye-gaze distribution, etc.

It is further conceivable to estimate the operator eye-gaze direction based on a plurality of eye-gaze direction hypotheses, wherein each hypothesis if represented, or embodied, in a respective eye-gaze distribution.

Furthermore, according to an exemplifying embodiment, the estimated operator eye-gaze direction, which is to be outputted by the method, is represented by a total eye-gaze direction distribution which is provided by combining the first and second, or plurality of, eye-gaze distributions.

According to an exemplifying embodiment, a saccade hypothesis is conceivable. For example, the method comprises detecting an operator body movement indicative of a saccade movement of the operator, and estimating a saccade eye-gaze distribution based on the detected operator body movement. For example, the saccade eye-gaze distribution forms the first eye-gaze distribution. The detected operator body movement may advantageously be a fast head movement which is indicative that the operator has performed a combined head and eye saccade involving a fast movement of head and a fast movement of eyes wherein the gaze direction of the operator's eyes is changed. For such combined head and eye saccade, the head movement and eye movement are interrelated. Hence, the detected operator body movement may for example by used for estimating a gaze direction based on the detected fast head movement.

According to an exemplifying embodiment of the third aspect, the step of estimating the operator eye-gaze direction further comprises determining a eye-gaze time value associated with a eye-gaze direction hypothesis, wherein the total eye-gaze direction distribution is determined based on the first and second, or plurality of, eye-gaze hypothesis and the eye-gaze time value.

According to a further exemplifying embodiment of the third aspect, a road-ahead hypothesis is conceivable. For example, the method may comprise estimating a road-ahead eye-gaze distribution which forms the second eye-gaze distribution. According to the method, the total eye-gaze direction distribution may further be determined based on the first and second, or plurality of, eye-gaze distributions and the eye-gaze time value. The time value allows for combining the different distributions into the total eye-gaze direction distribution by weighing the different distributions in relation to each other based on the eye-gaze time value.

According to yet an exemplifying embodiment, the operator motion input signal and estimated operator eye-gaze direction may be utilized for dead reckoning of the operator movement and eye-gaze direction during e.g. temporary tracking losses. Moreover, for certain situation, e.g. during the occurrence of specific operator eye-gaze direction hypothesis, or fast head or body movements of the operator, where it is expected that sensor data is only temporarily lost, the duration of the dead reckoning may be prolonged.

Moreover, according to various exemplifying embodiments of the present invention, it comprises monitoring noise levels in data signals provided by sensors and weighing the noise levels with confidence estimates from the sensors, e.g. represented by standard deviations. The operator motion input signal may further be monitored for detection of unrealistic, or un-physiological, behavior and movements of the operator, where unreliable data is discarded.

According to an exemplifying embodiment, the control means comprises a control unit and/or sub control units being arranged to communicate with each other and other systems, additional control units, and/or sensors in a vehicle via an internal vehicle communication network. Moreover, wireless communication between different vehicle, infrastructure and other devices is conceivable.

Furthermore, according to various embodiments, the control means may comprise a microprocessor, microcontroller, programmable digital signal processor or another programmable device. The control means may also, or instead, include an application specific integrated circuit, a programmable gate array or programmable array logic, a programmable logic device, or a digital signal processor. Where the control means includes a programmable device such as the microprocessor, microcontroller or programmable digital signal processor mentioned above, the processor may further include computer executable code that controls operation of the programmable device.

According to a another aspect of the present invention, a computer readable medium embodying a computer program product for determining a vehicle operator's visual input of an object in the operator's surroundings is provided, the computer program product comprising code configured to, when executed by a processor, receiving an object position signal indicative of the position of at least one object in the operator's surroundings; receiving an operator motion input signal indicative of physiological data comprising information relating to at least one of eye, face, head and body motion of the operator of the vehicle; estimating an operator eye-gaze direction based on the operator motion input signal; and determining a visual input quality value representative of level of visual input of the at least one object received by the operator, based on the object position signal and the estimated operator eye-gaze direction. The computer program may further, according to various exemplifying embodiments, comprise code configured operate according to the method, and/or embodiments thereof, according to the present invention.

The computer readable medium may be one of a removable nonvolatile random access memory, a hard disk drive, a floppy disk, a CD-ROM, a DVD-ROM, a USB memory, an SD memory card, or a similar computer readable medium known in the art.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing exemplary embodiments of the present invention, in which:

FIGS. 4a-c illustrate a side view, a top view and an operator's view, respectively, of objects appearing in the operator's environment.

DETAILED DESCRIPTION

Figure 1:
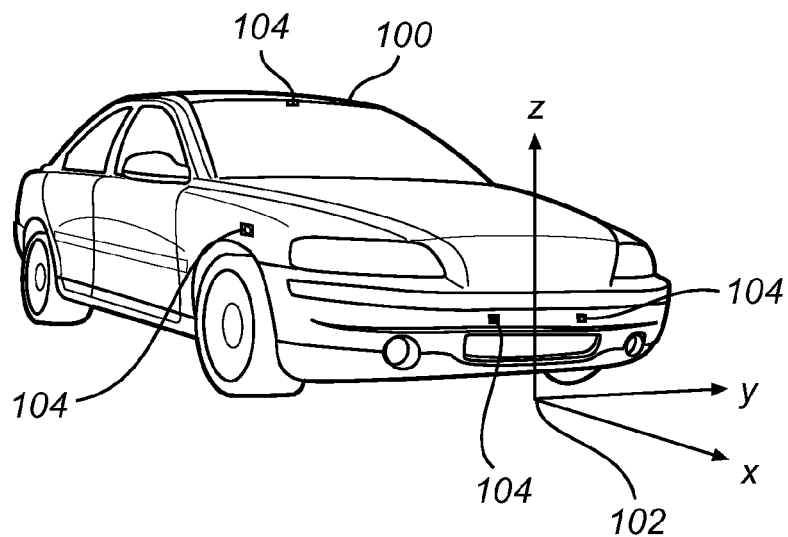
FIG. 1 is a perspective view of a vehicle equipped with external sensors and a coordinate system at its front end.

The present invention will now be described more fully hereinafter with reference to the accompanying drawings, in which exemplary embodiments of the invention are shown. This invention may, however, be embodied in many different forms and should not be construed as limited to the embodiments set forth herein; rather, these embodiments are provided for thoroughness and completeness. Like reference characters refer to like elements throughout.

In the following, the present invention is described with reference to a system for improving a visual input quality estimation of an operator of a vehicle. The vehicle is preferably equipped with interior sensor(s) for retrieving information of the vehicle operator and external sensor(s) for retrieving information of the vehicle operation as well as the surrounding environment of the vehicle. For the sake of better understanding, the internal and external sensors will now be described in relation to FIGS. 1-3.

FIG. 1 shows an exemplary vehicle, here illustrated as a car 100, in which a system according to the present invention may be incorporated. The car 100 is provided with external sensors 104 arranged to detect vehicle operation, such as overtaking, vehicle speed, vehicle yaw rate, etc, and objects, and zones, surrounding environment of the vehicle, e.g. lane markings, road marks, road curves, surrounding vehicles, etc. The external sensors 104 may be e.g. cameras or radar sensors. Preferably, a combination of camera and radar sensors may be used, since the camera provides a high precision when determining the height and width of the object, whereas a radar sensor provides a high precision when determining the distance to the object. Hereby, size, position, speed, etc. of the surrounding object can be determined. With reference to the position of the car 100, a coordinate system 102, here illustrated as a Cartesian coordinate system, is located at the front end of the car 100. The coordinate system 102 is arranged to follow the vehicle and the axis represent the longitudinal direction (x-axis), lateral direction (y-axis) and vertical direction (z-axis), respectively. The detected objects, in conjunction with the coordinate system 102 of the car 100, are provided to a system of the vehicle such that the system can determine the size and position of the object relative to the car 100. For example, the system may be continuously provided with object data from the different sensors 104. Hence it is also possible to determine speed and acceleration of surrounding traffic environment.

Figure 2:
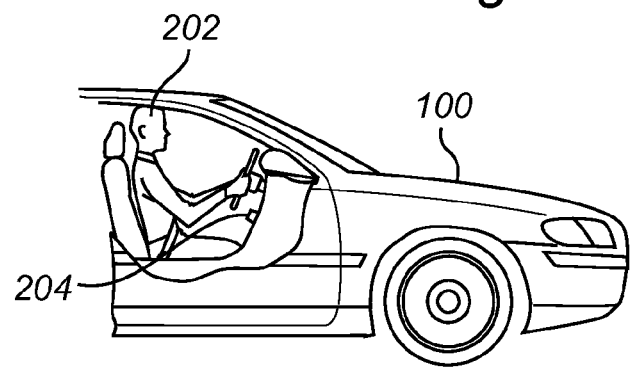
FIG. 2 is a perspective view of the interior of the vehicle, equipped with an internal sensor.

FIG. 2 illustrates an interior of a car 100 including a vehicle operator 202, wherein the vehicle 100 is equipped with an internal sensor, here illustrated as a camera system 204. The camera system 204 is arranged to measure and detect the behavior of the vehicle operator 202 during vehicle operation, and may be configured to generate an operator motion input signal indicative of physiological data comprising information relating to at least one of eye, face, head and body motion of the operator of the vehicle.

Furthermore, the camera system 204 may be arranged to focus on a predetermined number of positions of the operator's face, head, or upper body. These positions may, for example, be the eyes, eye-lids, eyebrows, nose, mouth, cheek, neck, shoulders, arms, etc. The camera system 204 may be pre-calibrated for a specific operator 202 normally operating the car or being calibrated each time an operator 202 enters the driver seat of the car 100. As the camera system 204 has detected the different positions of the operator's face or head, an estimation of facial behavior is possible for the camera system 204. The camera system 204 may hence detect, e.g. head and eye direction and movement, and derivative thereof, head pose, eye saccade, combined head and eye saccade, eye closure, speed of eye closure, etc.

Figure 3:
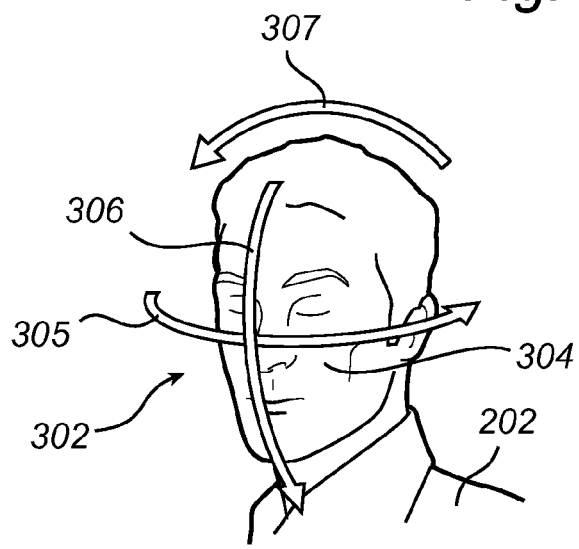
FIG. 3 illustrates a coordinate system of the face and head of a vehicle operator.

The camera system 204 may also, by use of a coordinate system 302 in connection to the operator's face 304, e.g. a operator-centric pitch/yaw coordinate system as illustrated in FIG. 3, detect if the head, or eyes, of the operator is rotating to the right or left (yaw), 305, rotating up or down (pitch), 306, or, in the case of the head movements, leaning towards the right or left shoulder (roll), 307. The coordinate system 302 of the face 304 is preferably a polar coordinate system with its origin positioned between the eyes of the operator.

Furthermore, the internal sensors may also, instead of, or additionally to the camera system 204, include other type of operator detecting means. This may, for example, be steering wheel sensors for detection of steering behavior, sensors in the acceleration pedal and/or braking pedal for detection of inconsistent acceleration and/or braking of the car 100, sensors in various buttons of the car 100 to detect if, for example, the operator 202 is adjusting any of the various functionalities of the infotainment system, etc. A still further internal sensor may be a breath analysis sensor or pupil size sensor for monitoring state of awareness of the operator.

Each object in the vehicle's environment is approximated by a 3D box with target corner points. Input data for objects are received in the following form per object. The data for each object, or zone, is described in the vehicle-based Cartesian coordinate system and contains corner position (including a standard deviation estimate) for each of the four corners in the X and Y directions, object height (including a standard deviation estimate) in the Z direction, object velocity and object acceleration.

In order to match objects with the operator's vision, the actual 3D world around the operator is divided into three views, a side view, a top view and an operator's view as shown in FIGS. 4 a-c, respectively. In FIG. 4c the operator's view is illustrated, comprising a road 1000, a truck 1001, a car 1002, a pedestrian 1003 and lane markings 1004. The side view and the top view are addressed separately to arrive at a description of the environment as seen from the operator's view. In the side and top views, the positions of the surrounding objects are described in the vehicle-based Cartesian coordinate system. This information is combined with the distance from the operator's head to the origin of the vehicle-based coordinate system, to calculate the yaw and pitch angles to the targets in the operator's head-based polar coordinate system.

The yaw ($\phi$) and pitch ($\theta$) angle calculations are done with the following equations:

$$\tan\varphi_1 = \frac{(y_{1,obj} - (y_{DMC} + y_{head}))}{(x_{1,obj} + x_{DMC} + x_{head})} \quad \tan\varphi_2 = \frac{(y_{2,obj} - (y_{DMC} + y_{head}))}{(x_{2,obj} + x_{DMC} + x_{head})}$$

$$\tan\varphi_3 = \frac{(y_{3,obj} - (y_{DMC} + y_{head}))}{(x_{3,obj} + x_{DMC} + x_{head})} \quad \tan\varphi_3 = \frac{(y_{4,obj} - (y_{DMC} + y_{head}))}{(x_{4,obj} + x_{DMC} + x_{head})}$$

In the equations $x_{n,obj}$ and $y_{n,obj}$ is the distance to object corner n in the X and Y directions, respectively and $x_{DMC}$, $y_{DMC}$ and $z_{DMC}$ is the distance from the origin of the vehicle's coordinate system to the sensor monitoring the operator in the respective directions, and $x_{head}$, $y_{head}$, and $z_{head}$ is the distance between the operator's head and the sensor monitoring the operator in the respective directions.

$$\tan\theta_1 = \frac{(h_{obj} - (z_{DMC} + z_{head}))}{(r_{1,obj} + x_{DMC} + x_{head})} \quad \tan\theta_2 = \frac{(h_{obj} - (z_{DMC} + z_{head}))}{(r_{2,obj} + x_{DMC} + x_{head})}$$

$$\tan\theta_3 = \frac{-(z_{DMC} + z_{head})}{(r_{3,obj} + x_{DMC} + x_{head})} \quad \tan\theta_4 = \frac{-(z_{DMC} + z_{head})}{(r_{4,obj} + x_{DMC} + x_{head})}$$

where $r_{n,obj} = \sqrt{(x_{n,obj}^2 + y_{n,obj}^2)}$ is the distance to object corner n and $h_{obj}$ is the height of the object.

Figure 4A:
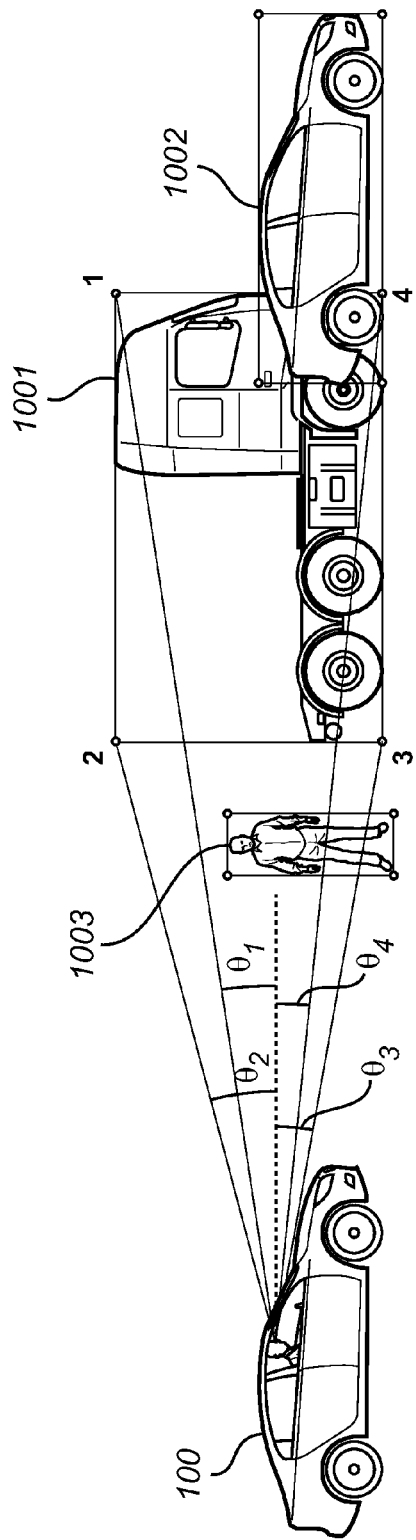
Figure 4B:
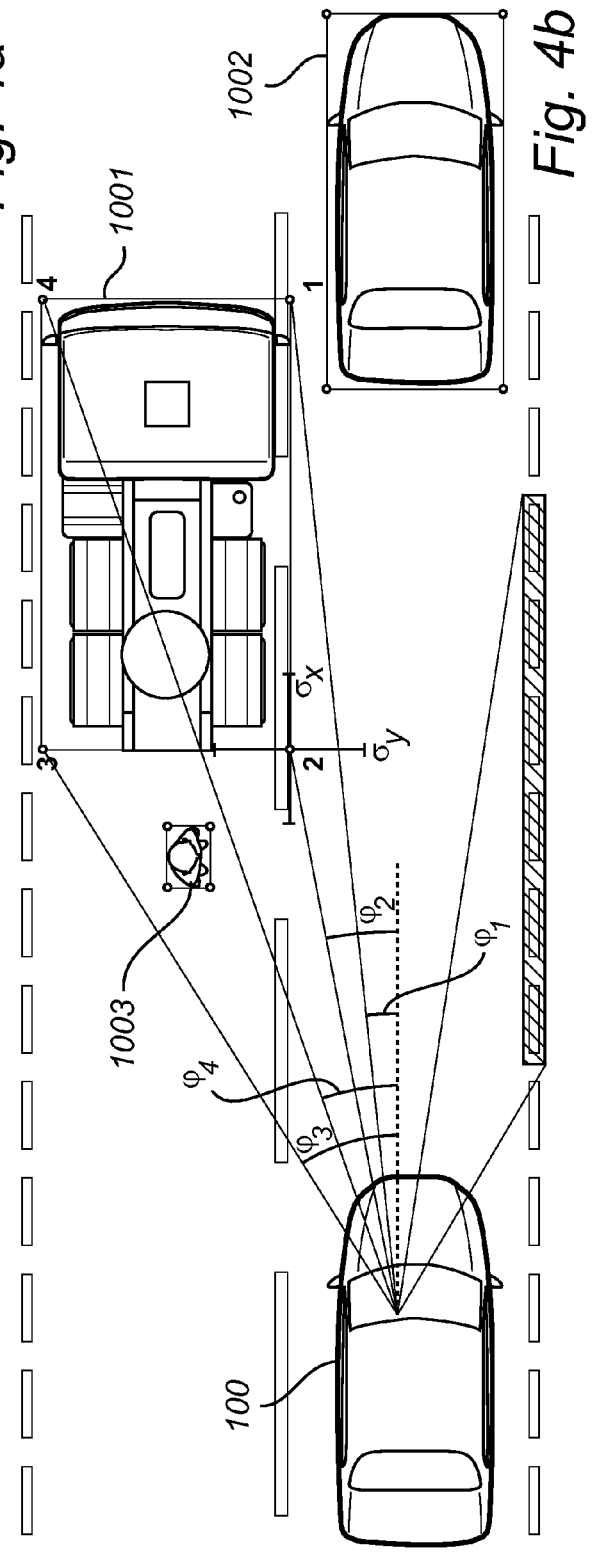

For sake of clarity, this has in FIGS. 4a-b only been illustrated for one of the objects, namely truck 1001. However, the same calculations are used for each object, such as for example the lane markings 1004, vehicles, pedestrians 1003, etc, in the surroundings of the vehicle.

Furthermore, in FIG. 4c, an object area 1005 of the truck 1001 is illustrated, which object area forms an approximated area in the operators visual field which corresponds to the truck 1001, wherein the object area is represented in driver centric pitch/yaw coordinate system. The object area is advantageously represented by rectangle area. The object area is, however, not limited to rectangular area. More accurate object areas which correspond to the actual shape of the object as perceived by the operator may be used in embodiments of the system and method according to the present invention.

As illustrated in FIG. 4b, with reference to corner point 2 of the object area of the truck 1001, the position of the corner points may be approximated by determining confidence intervals based on the signals from the external sensor systems. Confidence intervals are shown in the X and Y directions but are equally conceivable in the Z direction. The confidence intervals for the corner points may also be expressed in the in the driver's head-based polar coordinate system comprising yaw (φ) and pitch (θ). Furthermore, the method may involve using variance computations of the objects corner point in order to determine the objects position. For example, increased variance values imply that the uncertainty of the position of an object is increased which may be accounted for in the determination of the visual input quality value.

Figure 5:
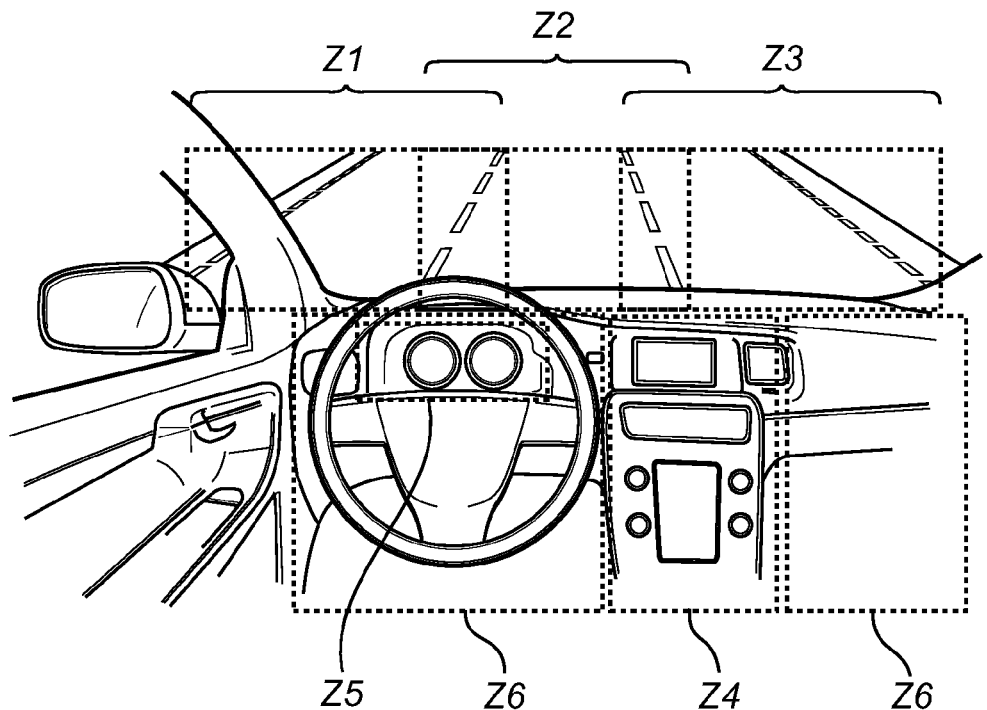
FIG. 5 illustrates an example of how zones ahead of and inside the vehicle may be defined.

Zones are defined and estimated as 2D or 3D objects, like any other object around, or inside, the vehicle. FIG. 5 shows an example of how zones ahead of and inside the vehicle could be defined. However, the figure only shows 2D objects (no X component) for simplicity in the visualization. The zones in FIG. 5 are just examples of how zones can be used, for some applications, zones at the side or rear of the vehicle can be useful.

As illustrated, the zones may overlap each other in the operator's view, such as zones Z1 corresponding to a left side road lane, Z2 corresponding to vehicle road lane, and Z3 corresponding to a right side road lane. An object may also be present in several zones at the same time. In such cases, the operator's visual input of the different zones may be weighted together, depending on how much of the object that is present in each zone.

Figure 6:
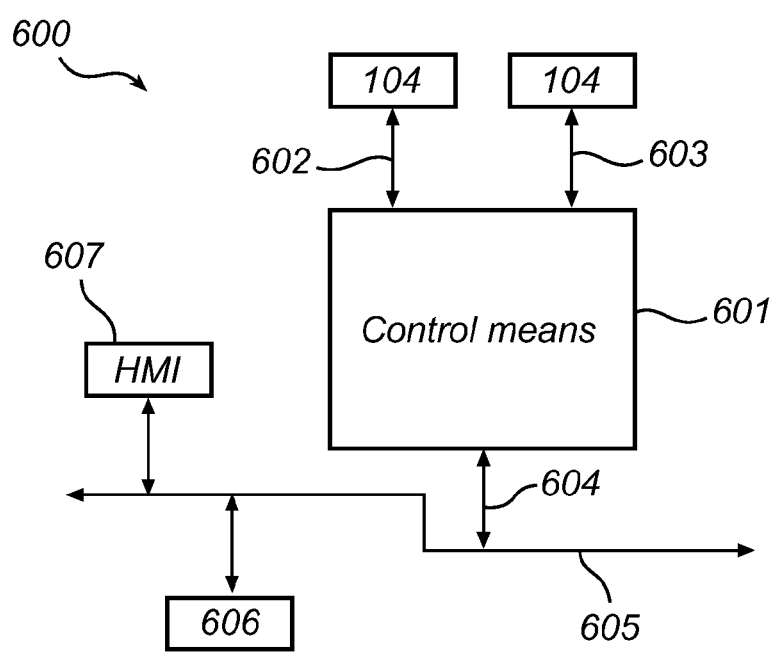
FIG. 6 schematically illustrates an embodiment of the system according to the present invention.

In FIG. 6 an embodiment of the system 600 for determining a vehicle operator's visual input of an object in the operator's surroundings according to the present invention, is schematically illustrated. The system 600 comprises control means 601 formed by a control unit which comprises two inputs 602 and 603. The first input 602 is arranged to receive an object position signal indicative of the position data of at least one object in the operator's surroundings, which position data is provide by an external sensor system 104. The second input 603 is arranged to receive an operator motion input signal indicative of physiological data comprising information relating to at least one of eye, face, head and body motion of the operator of the vehicle, wherein the physiological data is provided by an internal sensor system 204 monitoring the vehicle operator. The control unit of the control means 601 is further operatively connected to an in-vehicle communication network 605, such as CAN-BUS system or similar. Via the communication network 605 the control unit may communicate and provide information to and receive data from other in-vehicle systems 606, such as driver warning or driver assist systems, and interface device 607, such as human-machine interface device. According to an alternative embodiment, the control unit is operative connected to the external and internal sensor systems 104 and 204 via the communication network 605.

During operation, the control unit receives the object position signal and the operator motion input signal, and estimates an operator eye-gaze direction based on the operator motion input signal. The control unit further determines, and outputs via the communication network 605, a visual input quality value 604 representative of level of visual input of the at least one object received by the operator based on the object position signal and the estimated operator eye-gaze direction. In other words, the system receives information of an object or zone in the operator's surrounding and evaluates the operator's eye-gaze direction in order to assess and provide an estimate value indicative of how aware the operator is of the object, or of events occurring within the zone.

Figure 7:
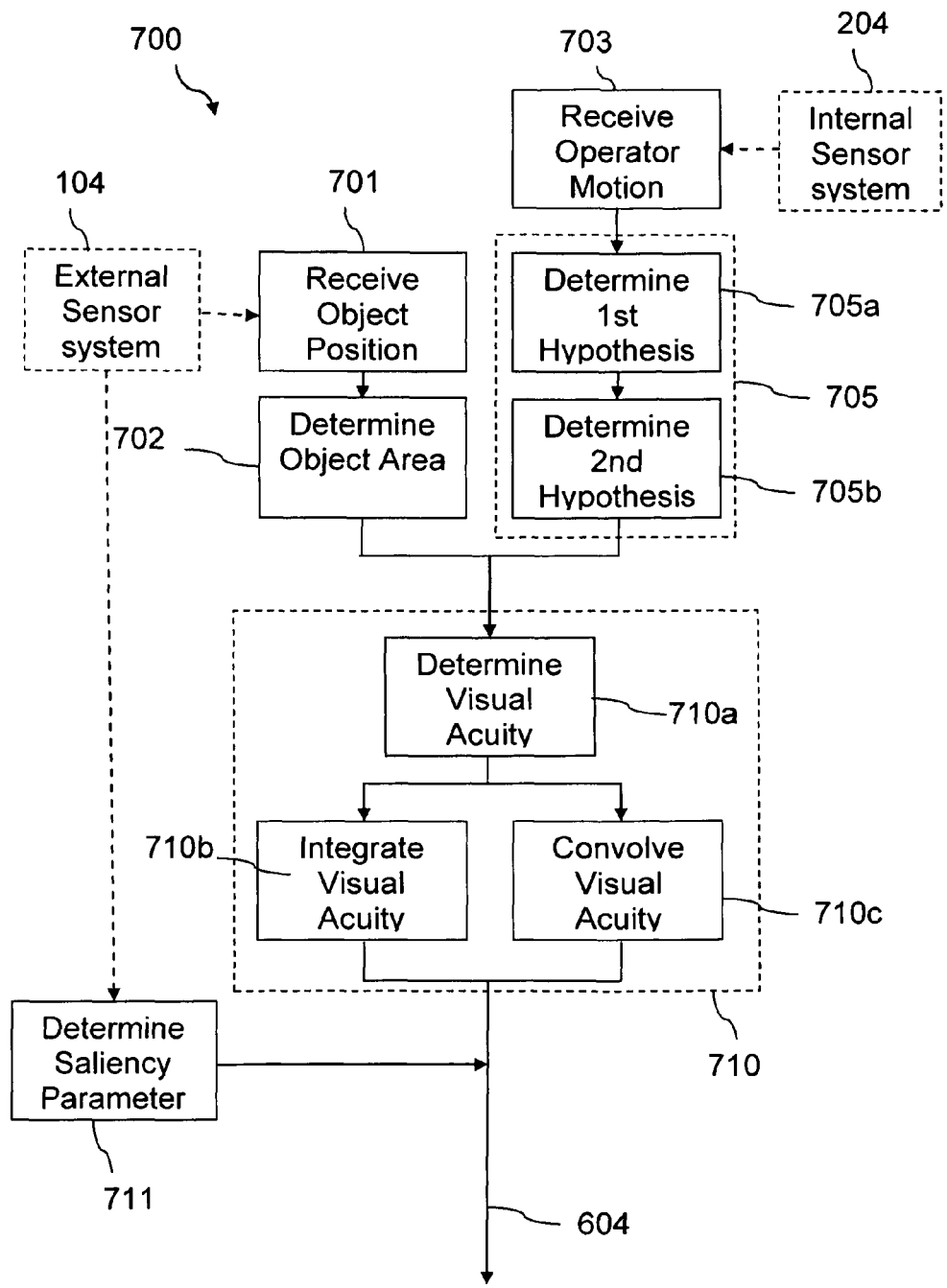
FIG. 7 illustrates a conceptual flow chart of an embodiment of the method according the present invention.

The control unit of the control means 602 may further be arranged to execute various embodiments of the method according to the present invention and as illustrated in FIG. 7.

For example, the control unit is arranged to determine an object area associated with the object, which object area is indicative of the object area of the object as perceived by the operator, wherein the visual input quality value is determined based on the object area. The control unit may further be arranged to determine a visual acuity distribution indicative of visual acuity level of an eye of the operator in relation to a center eye-gaze direction, wherein the visual input quality value is determined based on the visual acuity distribution.

In FIG. 7 a conceptual flow chart of various embodiments of the method 700 for determining a vehicle operator's visual input of an object in the operator's surroundings according the present invention, is illustrated. The method 700 comprises receiving, in step 701, an object position signal indicative of the position of at least one object in the operator's surroundings, which object position signal is provided by external sensor system 104, receiving, in step 703, an operator motion input signal indicative of physiological data comprising information relating to at least one of eye, face, head and body motion of the operator of the vehicle, which operator motion input signal is provided by internal sensor system 204;

estimating, in step 705, an operator eye-gaze direction comprising a total eye-gaze distribution based on the operator motion input signal; and determining, in step 710, a visual input quality value 604 representative of level of visual input of the at least one object received by the operator, based on the object position signal and the estimated operator eye-gaze direction.

Furthermore, the object position signal comprises information, such as coordinate points associated with the object, which are utilized to determine, in step 702, an object area associated with the at least one object, which object area is used to determine visual input quality value in step 710.

As further illustrated, the estimating 705 of the operator eye-gaze direction may comprise determining 705*a* a first eye-gaze direction hypothesis which represent an assumption of the eye-gaze direction of the operator. The method 700 further comprises determining 705*b* a second eye-gaze direction hypothesis which represent a different assumption of the eye-gaze direction of the operator. For example, the different hypotheses are based on physiological data comprising information relating to at least one of eye, face, head and body motion of the operator of the vehicle. An eye-gaze direction hypothesis may also be based on external events occurring in the operator's surroundings, such as movements of other vehicle. Hypothesis may also be based on the estimated correlations between different body movements of the operator, such as a combines head and eye saccade movement, wherein the eye-gaze direction is estimated based a detected head movement.

The step of determining the visual input quality value may, as illustrated, involve, in step 710*a*, determining a visual acuity distribution which is used in two separate steps 710*b* and 710*c* for determining the visual input quality value.

In more detail, the visual input quality value is determined, in step 710*b*, by integrating the visual acuity distribution over the total eye-gaze distribution over the object area. Hence, the visual input quality value is determined by placing the center point of the visual acuity distribution in each point in the object area and, for each point, weighing the complete visual acuity distribution in the object area with the total eye-gaze distribution in the object area, and summing the result for all the point in the object area into a visual input quality value.

In step 710*c*, the visual input quality value is determined by convolving the visual acuity distribution with the total eye-gaze distribution in the object area, such as resulting distribution indicative of visual input quality value is generated.

The outputted visual input quality value 604 may further be weighted by a saliency parameter value determined in step 711 based on the input signal from the external sensor system 104.

Figure 8:
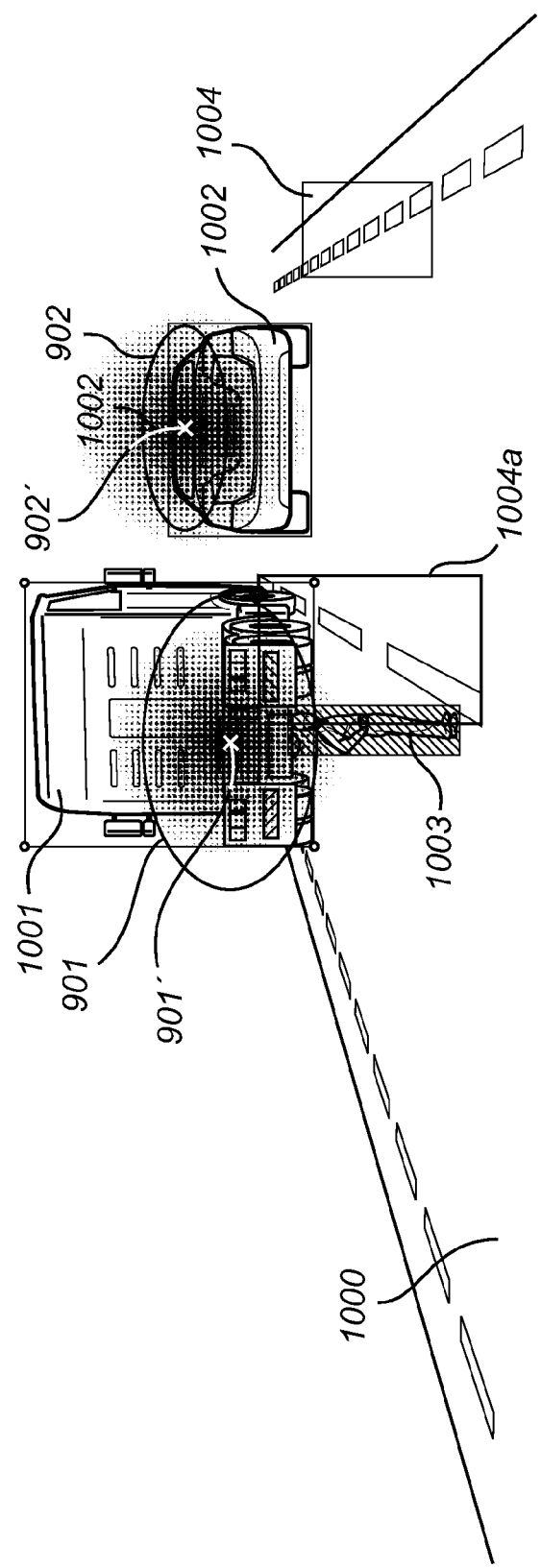
FIG. 8 schematically illustrates an operator view ahead of the vehicle during operation.

In FIG. 8, an operator view ahead of a vehicle during operation, which view corresponds to a typical traffic scene in the operator's view, is schematically illustrated. The operator's view comprises different objects, as described in relation to FIG. 4*c*, and left side and right side road lane markings 1004*a* and 1004*b*. Each object is further represented by an object area. A first and second eye-gaze direction distribution 901 and 902 are further illustrated.

The first eye-gaze distribution 901 is based on a saccade eye-gaze direction hypothesis wherein the eye-gaze direction is estimated based on e.g. a head movement of the operator which is indicative of a combined head and eye saccade. Hence, the eye-gaze direction according to the saccade eye-gaze direction hypothesis is the result of the most recent assumed combined head and eye saccade, and may be estimated by modeling the movement between operators head and eyes. As illustrated, according the to the saccade eye-gaze direction hypothesis, the operator's eye-gaze direction is aimed to the left wherein a peak point 901' of the saccade eye-gaze distribution is located in the object area of the truck 1001.

The second eye-gaze distribution 902 is based on a road-ahead eye-gaze hypothesis where the eye-gaze direction is assumed to be aimed in a road-ahead direction, which road-ahead may be different for different operators depending on e.g. body height and seating position, and may be determined by modeling the operator's movements during operation of the vehicle over time. As illustrated, according the to the road-ahead eye-gaze direction hypothesis, the operator's eye-gaze direction is aimed in a center direction, or a road-ahead far-point, in relation to the operators own road lane, wherein a peak point 902' of the saccade eye-gaze distribution is located in the object area of the car 1002.

Each separate eye-gaze distribution is typically represented by a probability distribution in pitch/yaw coordinates in relation to the operators. In order to provide the total eye-gaze distribution, the different distribution representing the different eye-gaze direction hypotheses may be suitably combined.

Figure 9:
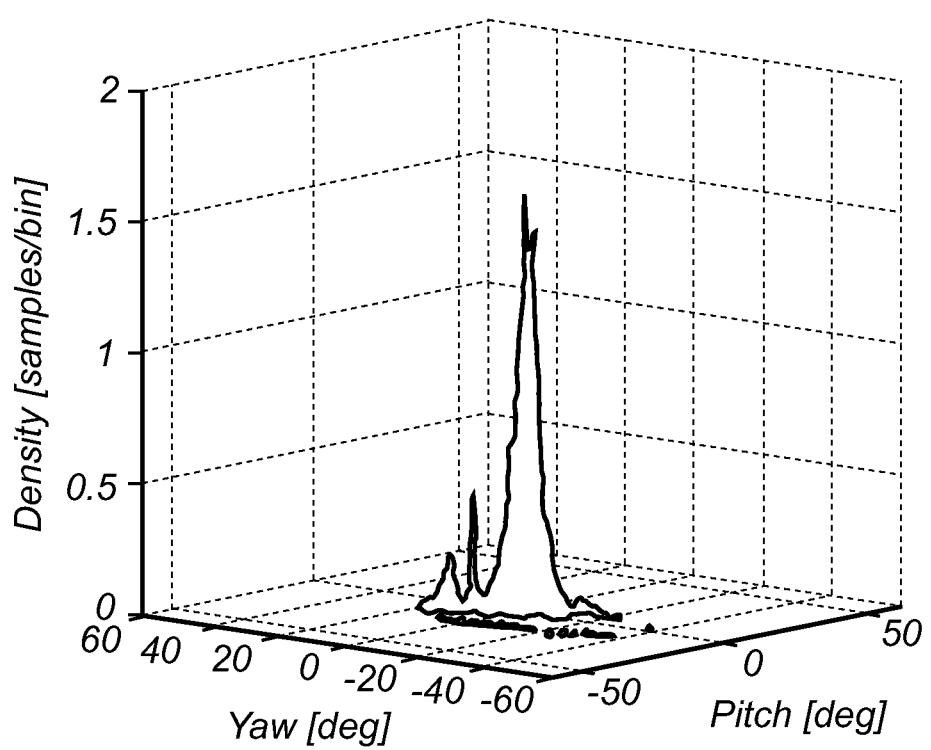
FIG. 9 illustrates a schematic plot of an estimated operator eye-gaze direction represented by an eye-gaze distribution.

For example, in FIG. 9, an estimated operator eye-gaze direction represented by a total eye-gaze distribution, is schematically plotted in a pitch/yaw and probability coordinate system. The total eye-gaze distribution is based on the plurality of different eye-gaze direction hypothesis, wherein the eye-gaze distributions of hypothesis are weighted together e.g. based on the eye-gaze time value. As illustrated, the pitch/yaw center point (0,0) comprises the highest probability peak. Hence, according to the total eye-gaze distribution representing the operator eye-gaze direction, the operator's eyes are most likely aimed in a straight forward direction, such as the road-ahead direction.

Figure 10:
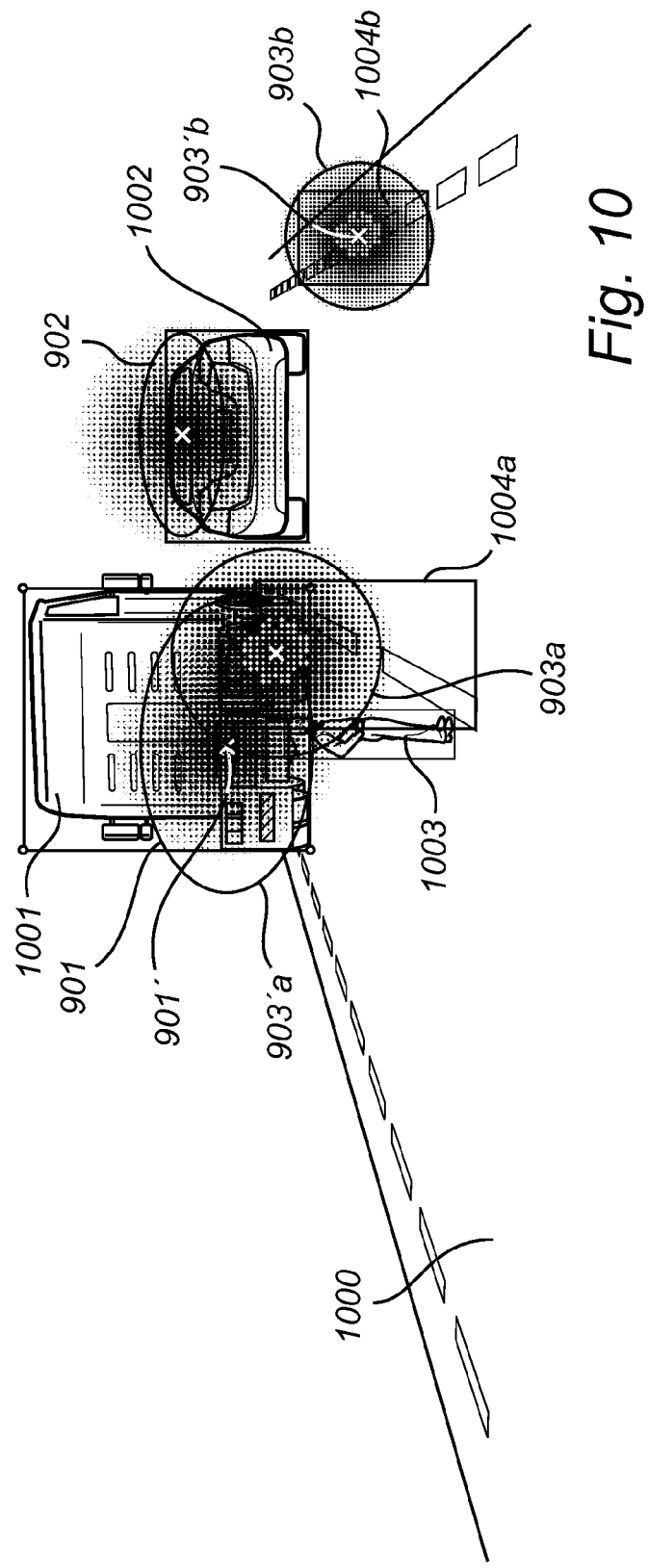
FIG. 10 schematically illustrates an operator view ahead of the vehicle during operation.

In FIG. 10, an operator view, as illustrated in FIG. 8, is shown, further comprising a first and a second exemplifying visual acuity distribution 903*a* and 903*b*, each representing a possible operator eye-gaze direction. The first distribution 903*a* corresponds to a center eye-gaze direction 903'*a* of the operator which is located within the truck 1001 object area and right side road lane marking 1004*a* object area. The second distribution 903*b* corresponds to a center eye-gaze direction 903' of the operator which is located within the right side road lane marking 1004*b* object area.

Even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims.

Furthermore, in the claims, the word "comprising" does not exclude other elements or steps, and the indefinite article "a" or "an" does not exclude a plurality.

The invention claimed is:

1. A method for determining a vehicle operator's visual input of an object in the operator's surroundings, the method comprising:
   receiving an object position signal indicative of a position of at least one object in the operator's surroundings;
   receiving an operator motion input signal indicative of physiological data comprising information relating to at least one of eye, face, head and body motion of the operator of the vehicle;
   estimating an operator eye-gaze direction based on the operator motion input signal;
   estimating an expected fixation probability indicative of a probability of fixation of the object by the operator's eyes; and
   determining a visual input quality value representative of a level of visual input of the at least one object received by the operator, based on the object position signal, the estimated operator eye-gaze direction, and the estimated expected fixation probability.

2. A method for determining a vehicle operator's visual input of an object in the operator's surroundings, the method comprising:

receiving an object position signal indicative of a position of at least one object in the operator's surroundings;

receiving an operator motion input signal indicative of physiological data comprising information relating to at least one of eye, face, head and body motion of the operator of the vehicle;

estimating an operator eye-gaze direction based on the operator motion input signal, in which the estimated operator eye-gaze direction comprises a total eye-gaze distribution indicative of a probability for different eye-gaze directions of the operator; and determining a visual input quality value representative of level of visual input of the at least one object received by the operator, based on the object position signal and the estimated operator eye-gaze direction.

3. A method according to claim 1, further comprising:
determining an object area associated with the object, the object area being indicative of the object as perceived by the operator, wherein the determining the visual input quality value is further based on the object area.

4. A method according to claim 3, in which the determining the visual input quality value comprises:
determining a visual acuity distribution indicative of visual acuity level of an eye of the operator in relation to a center eye-gaze direction; wherein the determining the visual input quality value is further based on the visual acuity distribution.

5. A method according to claim 4, in which the determining the visual input quality value comprises integrating the visual acuity distribution over the total eye-gaze distribution in the object area.

6. A method according to claim 4, in which the determining the visual input quality value comprises convolving the visual acuity distribution with the total eye-gaze distribution in the object area.

7. A method according to claim 1, further comprising:
determining a saliency parameter value associated with the object, the saliency parameter being indicative of a probability of attracting visual attention.

8. A method according to claim 2, further comprising:
determining a first eye-gaze direction hypothesis, wherein the total eye-gaze distribution is based on a first eye-gaze direction hypothesis.

9. A method according to claim 8, further comprising:
determining at least one second eye-gaze direction hypothesis; and
determining the total eye-gaze distribution by combining the first eye-gaze direction hypothesis and the at least one second eye-gaze direction hypothesis.

10. A method according to claim 2, in which the estimating the operator eye-gaze direction comprises:
detecting an operator body movement indicative of a saccade movement of the operator, and estimating a saccade eye-gaze distribution based on the detected operator body movement.

11. A method according to claim 10, in which the estimating the operator eye-gaze direction further comprises:
determining an eye-gaze time value associated with the saccade eye-gaze distribution, wherein the total eye-gaze distribution is determined based on the saccade eye-gaze distribution and the eye-gaze time value.

12. A method according to claim 11, in which the estimating the operator eye-gaze direction further comprises:
determining a road-ahead eye-gaze distribution, wherein the total eye-gaze distribution is determined by weighing the saccade eye-gaze distribution with the road-ahead eye-gaze distribution based on the eye-gaze time value.

13. A system for determining a vehicle operator's visual input of an object in the operator's surroundings, the system comprising:
a controller including,
a first input configured to receive an object position signal indicative of a position of at least one object in the operator's surroundings, and
a second input configured to receive an operator motion input signal indicative of physiological data comprising information relating to at least one of eye, face, head and body motion of the operator of the vehicle,
wherein the controller is configured to,
estimate an operator eye-gaze direction based on the operator motion input signal,
estimate an expected fixation probability indicative of a probability of fixation of the object by the operator's eyes, and
determine a visual input quality value representative of a level of visual input of the at least one object received by the operator, based on the object position signal, the estimated operator eye-gaze direction, and the estimated expected fixation probability.

14. A non-transitory computer readable medium embodying a computer program product for determining a vehicle operator's visual input of an object in the operator's surroundings, the computer program product comprising code configured to, when executed by a processor, perform the operations of:
receiving an object position signal indicative of a position of at least one object in the operator's surroundings;
receiving an operator motion input signal indicative of physiological data comprising information relating to at least one of eye, face, head and body motion of the operator of the vehicle;
estimating an operator eye-gaze direction based on the operator motion input signal;
estimating an expected fixation probability indicative of a probability of fixation of the object by the operator's eyes; and
determining a visual input quality value representative of level of visual input of the at least one object received by the operator, based on the object position signal, the estimated operator eye-gaze direction, and the estimated expected fixation probability.

15. A system for determining a vehicle operator's visual input of an object in the operator's surroundings, the system comprising:
a controller including,
a first input configured to receive an object position signal indicative of a position of at least one object in the operator's surroundings, and
a second input configured to receive an operator motion input signal indicative of physiological data comprising information relating to at least one of eye, face, head and body motion of the operator of the vehicle,
wherein the controller is configured to,
estimate an operator eye-gaze direction based on the operator motion input signal, in which the estimated operator eye-gaze direction comprises a total eye-gaze distribution indicative of a probability for different eye-gaze directions of the operator, and
determine a visual input quality value representative of a level of visual input of the at least one object received by the operator, based on the object position signal and the estimated operator eye-gaze direction.

16. A non-transitory computer readable medium embodying a computer program product for determining a vehicle operator's visual input of an object in the operator's surroundings, the computer program product comprising code configured to, when executed by a processor, perform the operations of:
receiving an object position signal indicative of a position of at least one object in the operator's surroundings;
receiving an operator motion input signal indicative of physiological data comprising information relating to at least one of eye, face, head and body motion of the operator of the vehicle;
estimating an operator eye-gaze direction based on the operator motion input signal, in which the estimated operator eye-gaze direction comprises a total eye-gaze distribution indicative of a probability for different eye-gaze directions of the operator; and
determining a visual input quality value representative of level of visual input of the at least one object received by the operator, based on the object position signal and the estimated operator eye-gaze direction.

* * * * *